(12) United States Patent
Mitsuzawa et al.

(10) Patent No.: US 8,609,376 B2
(45) Date of Patent: Dec. 17, 2013

(54) PROCESS FOR PRODUCING SACCHARIFIED SOLUTION OF LIGNOCELLULOSIC BIOMASS

(75) Inventors: Shigenobu Mitsuzawa, Saitama (JP); Minako Onodera, Saitama (JP); Maiko Fukuura, Saitama (JP); Koh Shikata, Hyogo (JP); Yasuhiro Kashima, Hyogo (JP)

(73) Assignees: Honda Motor Co., Ltd., Tokyo (JP); Thermostable Enzyme Laboratory Co., Ltd., Kobe (JP)

( * ) Notice: Subject to any disclaimer, the term of this patent is extended or adjusted under 35 U.S.C. 154(b) by 256 days.

(21) Appl. No.: 13/103,568

(22) Filed: May 9, 2011

(65) Prior Publication Data

US 2012/0003702 A1 Jan. 5, 2012

(30) Foreign Application Priority Data

Jun. 30, 2010 (JP) ................. 2010-149434

(51) Int. Cl.
*C12P 19/14* (2006.01)
(52) U.S. Cl.
USPC ............................................. 435/99
(58) Field of Classification Search
USPC .................................................. 435/99
See application file for complete search history.

(56) References Cited

U.S. PATENT DOCUMENTS 7,923,236 B2 * 4/2011 Gusakov et al. ............. 435/209
8,034,596 B2 * 10/2011 Fang et al. .................... 435/195

FOREIGN PATENT DOCUMENTS

JP 2009-171952 A 8/2009

OTHER PUBLICATIONS

Xue et al. [Biotechnology Letters 26: 1511-1515 (2004)].*
Wyman et al. Bioresource Technology 96 (2005) 1959-1966.*

* cited by examiner

*Primary Examiner* — Tekchand Saidha
(74) *Attorney, Agent, or Firm* — Arent Fox LLP

(57) ABSTRACT

A process for producing a saccharified solution, by which xylose can be produced at a high yield from lignocellulosic biomass, is provided. The saccharification is carried out by adding a saccharifying enzyme to a pretreated material for saccharification of the lignocellulosic biomass. As the saccharifying enzyme is added a mixture of a first saccharifying enzyme originated from one or more microorganisms selected from the group consisting of fungi of the genus *Acremonium*, the genus *Trichoderma*, the genus *Penicillium*, the genus *Aspergillus* and the genus *Thermoascus*, and eubacteria of the genus *Clostridium* and the genus *Bacillus*, and a second saccharifying enzyme composed of β-xylosidase originated from *Thermotoga maritima*.

9 Claims, 3 Drawing Sheets

PROCESS FOR PRODUCING SACCHARIFIED SOLUTION OF LIGNOCELLULOSIC BIOMASS

BACKGROUND OF THE INVENTION

1. Field of the Invention

The present invention relates to a process for producing a saccharified solution of lignocellulosic biomass.

2. Description of the Related Art

Conventionally, a process for producing ethanol by saccharifying lignocellulosic biomass, such as rice straw, as a substrate by a saccharifying enzyme produced by a microorganism and fermenting the yielded saccharides, has been known. The lignocellulosic biomass is constituted so that lignin is tightly bound to cellulose or hemicellulose. Consequently, for the saccharification is used a pretreated material for saccharification, which is the lignocellulosic biomass so pretreated that lignin contained in the lignocellulosic biomass is dissociated or the lignocellulosic biomass is swollen.

The term "dissociated" means herein that the bonds between lignin and cellulose or hemicellulose are at least partly cleaved. The term "swollen" means that a liquid penetrates between cellulose or hemicellulose constituting crystalline cellulose to generate gaps, or gaps are generated in a cellulose fiber, to expand the crystalline cellulose.

According to the conventional process for producing ethanol, the concentration of the substrate contained in the pretreated material for saccharification is often limited to a low level in order to reduce the consumption of the saccharifying enzyme, because the saccharifying enzyme is so expensive. Meanwhile, in case the concentration of the substrate contained in the pretreated material for saccharification is low, the concentration of the saccharified solution obtained from such a pretreated material for saccharification becomes also low, and consequently the concentration of the ethanol obtained by fermenting the saccharified solution becomes also low. As a result, there has been a problem that the time and thermal energy required for distillation in order to concentrate the obtained ethanol would increase.

To solve the problem, it is conceivable to increase the concentration of the substrate contained in the pretreated material for saccharification and the consumption of the saccharifying enzyme so as to obtain ethanol at a higher concentration. In this case, however, to cope with the cost increase due to the increase in the consumption of the expensive saccharifying enzyme, the total cost of the production process for ethanol needs to be curtailed.

One of the measures to curtail the cost in the production process for ethanol may be improvement of the efficiency of the saccharifying treatment of lignocellulosic biomass.

A process for producing monosaccharides such as glucose has been known, in which cellulose or hemicellulose constituting a cell wall of the lignocellulosic biomass is hydrolyzed using a saccharifying enzyme. By the process, monosaccharides, such as xylose, mannose and arabinose, originated from hemicellulose can be produced in addition to glucose.

For the improvement of the efficiency of the saccharifying treatment of lignocellulosic biomass, it is desirable to increase the yield of various monosaccharides including xylose in addition to glucose. In this regard, a combined use of a plurality of saccharifying enzymes in the saccharifying treatment of the lignocellulosic biomass has been known as effective (see e.g. Japanese Patent Application Laid-Open Publication No. 2009-171952).

There occurs, however, a disadvantage that the activity of a saccharifying enzyme, especially a saccharifying enzyme that hydrolyzes xylan to yield xylose, is inhibited in accordance with the increase in the produced amount of xylose, when lignocellulosic biomass is saccharified by the saccharifying enzyme. As a result, the yield of xylose is decreased, and the saccharifying treatment of lignocellulosic biomass cannot be improved sufficiently.

SUMMARY OF THE INVENTION

An object of the present invention is to provide a process for producing a saccharified solution, by which the disadvantage is resolved, the activity of a saccharifying enzyme is hardly inhibited even if the produced amount of xylose is increased, when lignocellulosic biomass is saccharified by a saccharifying enzyme, and xylose can be produced at a high yield from a substrate mixture including the lignocellulosic biomass.

To attain the object, the process for producing a saccharified solution of lignocellulosic biomass according to the present invention comprises preparation of a pretreated material for saccharification by pretreating lignocellulosic biomass as a substrate to dissociate lignin contained in the lignocellulosic biomass or swell the lignocellulosic biomass, and a saccharifying treatment of a substrate-saccharifying enzyme mixture obtained by adding a saccharifying enzyme produced by a microorganism to the pretreated material for saccharification with the saccharifying enzyme to produce a saccharified solution, wherein a mixture of a first saccharifying enzyme comprising a saccharifying enzyme originated from one or more microorganisms selected from the group consisting of fungi of the genus *Acremonium*, the genus *Trichoderma*, the genus *Penicillium*, the genus *Aspergillus* and the genus *Thermoascus*, and eubacteria of the genus *Clostridium* and the genus *Bacillus*, and a second saccharifying enzyme comprising β-xylosidase originated from *Thermotoga maritima* is added as the saccharifying enzyme.

The first saccharifying enzyme contains cellulase or hemicellulase produced by the microorganism.

By the process for producing a saccharified solution according to the present invention, a monosaccharide, such as glucose and xylose, can be produced by saccharifying lignocellulosic biomass as a substrate by adding a mixture of the first saccharifying enzyme and the second saccharifying enzyme as the saccharifying enzyme. In this case, through the use of the second saccharifying enzyme together with the first saccharifying enzyme, the inhibition of the activities of the first saccharifying enzyme and the second saccharifying enzyme due to the increase in the production amount of xylose can be suppressed.

As a result, xylose can be produced from the lignocellulosic biomass as the substrate at a high yield by the process for producing a saccharified solution according to the present invention.

The substrate-saccharifying enzyme mixture in the process for producing a saccharified solution according to the present invention contains preferably the substrate at a concentration in the range of 10 to 26% by mass.

In case the substrate concentration is less than 10% by mass, a saccharified solution with a sufficiently high saccharide concentration may not be occasionally obtained. Meanwhile, it is technically difficult to elevate the substrate concentration beyond 26% by mass.

The substrate-saccharifying enzyme mixture in the process for producing a saccharified solution according to the present invention contains preferably the first saccharifying enzyme at a concentration in the range of 0.1 to 10% by mass, as well as the second saccharifying enzyme at a concentration in the range of 0.06 to 1.0% by mass.

In case the concentration of the first saccharifying enzyme contained in the substrate-saccharifying enzyme mixture is less than 0.1% by mass and the concentration of the second saccharifying enzyme is less than 0.06% by mass, the substrate may not be sufficiently saccharified, and the suppressing activity on the inhibition of the enzyme activity due to the increase in the production amount of xylose may not be obtained adequately. Meanwhile, in case the concentration of the first saccharifying enzyme contained in the substrate-saccharifying enzyme mixture exceeds 10% by mass and the concentration of the second saccharifying enzyme exceeds 1.0% by mass, the suppressing activity on the inhibition of the enzyme activity due to the increase in the production amount of xylose may not be promoted further.

DETAILED DESCRIPTION OF THE PREFERRED EMBODIMENTS

Figure 1:
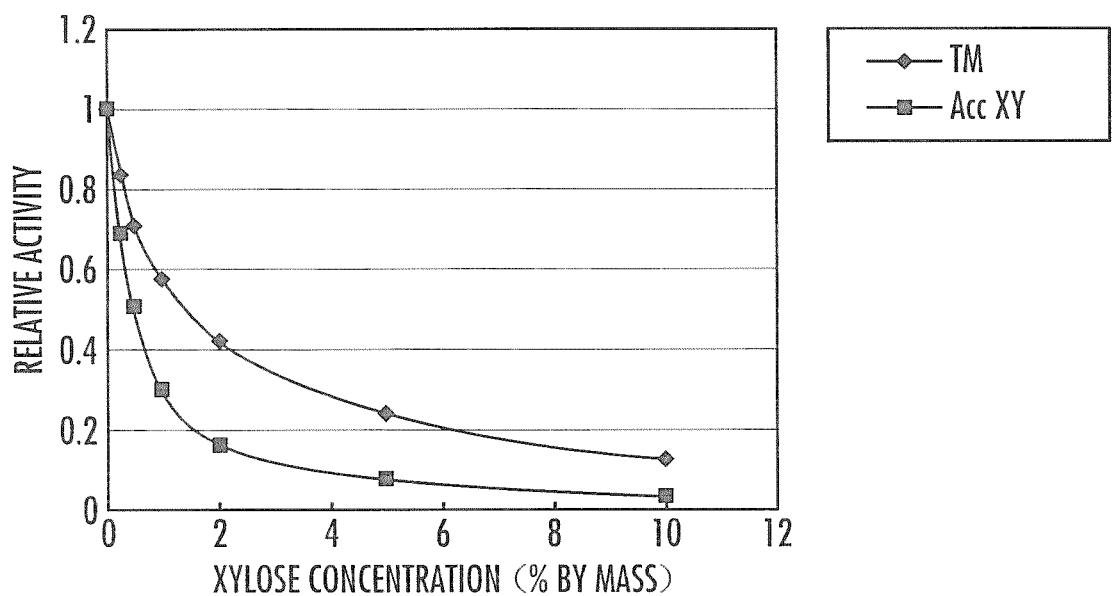
FIG. 1 is a graph showing the relationship between the relative activity of the first saccharifying enzyme or the second saccharifying enzyme and the xylose concentration.

Embodiments of the present invention will now be described in more detail referring to the accompanying figures.

According to a process for producing a saccharified solution of the present embodiment, a saccharified solution is produced by preparing a pretreated material for saccharification by pretreating lignocellulosic biomass as a substrate to dissociate lignin contained in the lignocellulosic biomass or swell the lignocellulosic biomass, and a saccharifying treatment of a substrate-saccharifying enzyme mixture obtained by adding a saccharifying enzyme produced by a microorganism to the pretreated material for saccharification with the saccharifying enzyme. In such event, a mixture of the first saccharifying enzyme comprising a saccharifying enzyme originated from one or more microorganisms selected from the group consisting of fungi of the genus *Acremonium*, the genus *Trichoderma*, the genus *Penicillium*, the genus *Aspergillus* and the genus *Thermoascus*, and eubacteria of the genus *Clostridium* and the genus *Bacillus*, and the second saccharifying enzyme comprising β-xylosidase originated from *Thermotoga maritima* is added to the pretreated material for saccharification as the saccharifying enzyme.

Examples of lignocellulosic biomass to be used as the substrate include wood, rice straw, wheat straw, bagasse, bamboo, pulp, and wastes thereof such as used paper, and rice straw can be favorably used. The lignocellulosic biomass is so constituted that lignin is tightly bound to cellulose or hemicellulose. Consequently, according to a process for producing a saccharified solution of the present embodiment, ammonia water is mixed with the lignocellulosic biomass to prepare firstly the substrate mixture as a mixture of the lignocellulosic biomass and the ammonia water.

Then, the substrate mixture is maintained at a temperature in the range of 20 to 100° C., e.g. at 80° C., for a duration in the range of 0.5 to 24 hours. e.g. for 8 hours, to react the lignocellulosic biomass with the ammonia water. Thus a pretreated material for saccharification, in which lignin contained in the lignocellulosic biomass is dissociated or the lignocellulosic biomass is swollen, can be prepared.

Since the pretreated material for saccharification contains ammonia, the ammonia is then vaporized to ammonia gas to separate the same from the pretreated material for saccharification. Then a saccharifying enzyme is added to the pretreated material for saccharification freed of the ammonia gas to prepare a substrate-saccharifying enzyme mixture.

The substrate-saccharifying enzyme mixture should preferably contain the lignocellulosic biomass as a substrate at a concentration in the range of 10 to 26% by mass. In case the substrate-saccharifying enzyme mixture contains the lignocellulosic biomass at a concentration less than 10% by mass, a saccharified solution with a sufficiently high saccharide concentration may not be obtained by the treatment with the saccharifying enzyme. Meanwhile, it is technically difficult to elevate the concentration of the lignocellulosic biomass in the substrate-saccharifying enzyme mixture beyond 26% by mass.

The first saccharifying enzyme added in the substrate-saccharifying enzyme mixture contains cellulase or hemicellulase produced by the fungi or the eubacteria. Examples of the first saccharifying enzyme include a saccharifying enzyme originated from a microorganism of the genus *Acremonium* (by Meiji Seika Kaisha, Ltd., Trade name: *Acremonium* cellulase) and a saccharifying enzyme originated from a microorganism of the genus *Trichoderma* (by Genencor, a division of Danisco US Inc., Trade name: GC220).

The second saccharifying enzyme is comprised of β-xylosidase produced by a bacterium *Thermotoga maritima*.

According to a process for producing a saccharified solution of the present embodiment, as the β-xylosidase originated from *Thermotoga maritima*, DNA encoding the β-xylosidase produced by *Thermotoga maritima* is amplified by PCR and cloned and expressed in *E. coli* so as to function as a gene, and the product can be purified and used.

Although as an *E. coli* expression promoter, a promoter induced by isopropyl-β-thiogalactopyranoside can be used, other inducible promoters or constitutive promoters can be used, insofar as the production of β-xylosidase is not disturbed. Further, a host to produce β-xylosidase is not limited to *E. coli*, and other bacteria such as *Bacillus subtilis*, fungi such as yeast and filamentous fungi, and animal cells such as a Chinese hamster ovary cell (CHO cell) can be used.

Although β-xylosidase expressed by a functioning gene cloned in *E. coli* can be used according to the production process of the present embodiment, β-xylosidase produced by *Thermotoga maritima* itself may be also used after purification without cloning.

Examples of β-xylosidase originated from *Thermotoga maritima* as the second saccharifying enzyme include β-xylosidase from Thermostable Enzyme Laboratory Co. Ltd.

According to the production process of the present embodiment, the substrate-saccharifying enzyme mixture contains the first saccharifying enzyme at a concentration in the range of 0.1 to 10% by mass, preferably 0.9 to 1.10% by mass, as well as the second saccharifying enzyme preferably at a concentration in the range of 0.06 to 1.0% by mass.

Then, according to the production process of the present embodiment, the substrate-saccharifying enzyme mixture is maintained at a temperature in the range of 20 to 60° C. e.g. at 50° C. for a duration in the range of 24 to 240 hours, e.g. for 3 days, for saccharification. Therethrough, the lignocellulosic biomass is hydrolyzed by the first saccharifying enzyme and the second saccharifying enzyme, and a saccharified solution containing saccharides, such as glucose, and xylose, can be produced.

In this case, according to the production process of the present embodiment, through the use of a mixture of the first saccharifying enzyme and the second saccharifying enzyme, the inhibition of the enzyme activity is suppressed, even if the product amount of xylose increases, and thus xylose can be obtained at a high yield.

In case the concentration of the first saccharifying enzyme contained in the substrate-saccharifying enzyme mixture is less than 0.1% by mass and the concentration of the second saccharifying enzyme is less than 0.06% by mass, the substrate may not be saccharified sufficiently, and the suppressing activity of the inhibition of the enzyme activity due to the increase in the product amount of xylose may not be obtained sufficiently. In case the concentration of the first saccharifying enzyme contained in the substrate-saccharifying enzyme mixture exceeds 10% by mass and the concentration of the second saccharifying enzyme exceeds 1.0% by mass, the suppressing activity on the inhibition of the enzyme activity due to the increase in the product amount of xylose may not be promoted further.

The change in the enzyme activity with the concentration of xylose is shown in FIG. 1 with respect to β-xylosidase originated from *Thermotoga maritima* (by Thermostable Enzyme Laboratory Co., Ltd.) and commercially available xylanase (by Genencor, a division of Danisco US Inc., Trade name: Accellerase XY). In FIG. 1 the expression "TM" means the β-xylosidase originated from *Thermotoga maritima*, and the expression "Acc XY" means the commercial xylanase.

The change in the enzyme activity with the concentration of xylose is measured with a sample solution containing 1 mM 4-nitrophenyl β-D-xylopyranoside as a substrate, 0.2 M sodium acetate buffer solution (pH 4.0) and xylose at a predetermined concentration. There are 7 sample solutions, which respectively contain xylose at nil % by mass, 0.25% by mass, 0.5% by mass, 1% by mass, 2% by mass, 5% by mass, and 10% by mass.

For the measurement, each sample solution is heated to 50° C. thereto is added the β-xylosidase originated from *Thermotoga maritima* or the commercial xylanase, the resulting solution is incubated at 50° C. for 10 minutes, thereto is added a 0.25 M sodium carbonate solution twice as much as each sample solution, and after terminating the reaction a color reaction is carried out. Then the absorbance of light at a wavelength of 420 nm by each sample solution is measured by a spectrophotometer to determine the enzyme activity of the β-xylosidase originated from *Thermotoga maritima* or the commercial xylanase.

In the measurement, the β-xylosidase originated from *Thermotoga maritima* is added into each sample solution to $1.3 \times 10^{-2}$ U/mL. The commercial xylanase is added into each sample solution to $1.1 \times 10^{-2}$ U/mL. Herein 1 U is defined as the enzyme quantity to yield 1 μmol per minute of 4-nitrophenol from 4-nitrophenyl β-D-xylopyranoside as a substrate.

The enzyme activity is expressed by a relative activity value with respect to each enzyme activity of the β-xylosidase originated from *Thermotoga maritima* or the commercial xylanase for a sample solution not containing any xylose as defined as 1.

As shown in FIG. 1 there is a tendency that the relative activity decreases with the increase of the xylose concentration for both the β-xylosidase originated from *Thermotoga maritima* and the commercial xylanase. The tendency of decrease in the relative activity is milder for the β-xylosidase originated from *Thermotoga maritima*. This means that the inhibition intensity of the enzyme activity by xylose is weaker on the β-xylosidase originated from *Thermotoga maritima* than on the commercial xylanase.

Figure 2:
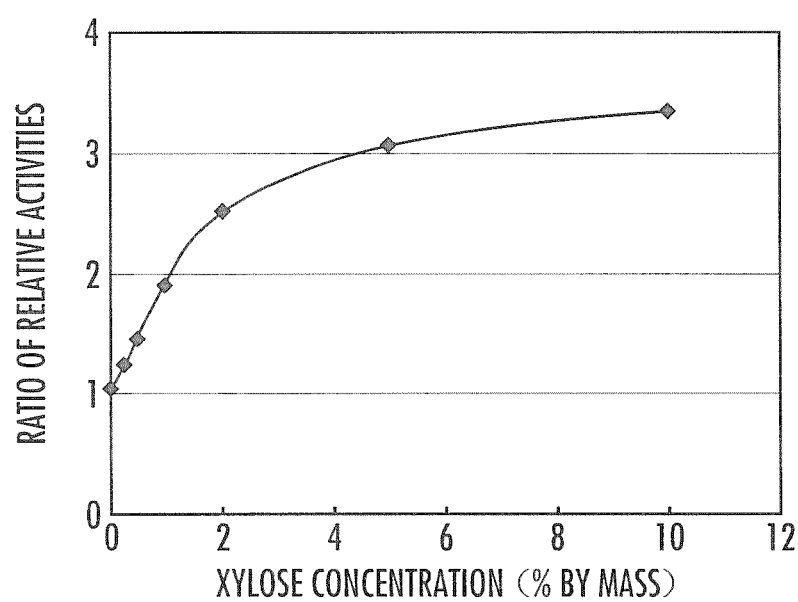
FIG. 2 is a graph showing the relationship between the ratio of the relative activity of the second saccharifying enzyme to the relative activity of the first saccharifying enzyme and the xylose concentration.

FIG. 2 shows the relationship between the ratio of the relative activity of the β-xylosidase originated from *Thermotoga maritima* to the relative activity of the commercial xylanase and the xylose concentration.

As shown in FIG. 2, the β-xylosidase originated from *Thermotoga maritima* has the activity 2.5 to 3-fold the activity of the commercial xylanase or even higher, in a xylose concentration range of 2% by mass or higher. This indicates that in saccharifying a substrate-saccharifying enzyme mixture containing the lignocellulosic biomass as the substrate, the addition of the β-xylosidase originated from *Thermotoga maritima* can suppress the inhibition of the enzyme activity of the β-xylosidase, even if the product amount of xylose is increased, and enable production of xylose at a high yield.

The high yield of xylose means also that degradation of hemicellulose existing in the lignocellulosic biomass as entangled with cellulose is promoted. If degradation of hemicellulose is promoted, the entanglement between cellulose and hemicellulose is disentangled and cellulase is expected to be adsorbed easily on cellulose surfaces.

Consequently, it can be expected that production of xylose as well as degradation of cellulose are promoted and the concentration of total saccharides in an obtained saccharified solution is increased by the saccharifying enzyme, prepared by adding the second saccharifying enzyme composed of β-xylosidase originated from *Thermotoga maritima* to the first saccharifying enzyme composed of a saccharifying enzyme originated from one or more microorganisms selected from the group consisting of fungi of the genus *Acremonium*, the genus *Trichoderma*, the genus *Penicillium*, the genus *Aspergillus* and the genus *Thermoascus*, and eubacteria of the genus *Clostridium* and the genus *Bacillus*.

Examples and Comparative Examples of the present invention will be described below.

Example 1

In the current Example a saccharified solution was produced as follows.

Firstly, air-dried rice straw was crushed by a cutter mill and passed through a screen filter 3 mm in diameter to prepare crushed rice straw. Then the crushed rice straw was mixed with 25% by mass-ammonia water at a mass ratio of 1:4 to obtain a substrate mixture. The substrate mixture was maintained at a temperature of 80° C. for 8 hours to react the crushed rice straw with the ammonia water to dissociate lignin contained therein or swell the crushed rice straw, and thus a pretreated material for saccharification was prepared. Then the pretreated material for saccharification was air-dried to remove ammonia from the pretreated material for saccharification to prepare ammonia-treated rice straw.

Next, the ammonia-treated rice straw was suspended in an acetate buffer solution (pH 4). To the prepared suspension a saccharifying enzyme originated from a microorganism of the genus *Acremonium* (by Meiji Seika Kaisha. Ltd. Trade name: *Acremonium* cellulase) was added as the first saccharifying enzyme to an effective protein concentration of 1.1% by mass with respect to the total amount of the suspension. To the suspension added with the saccharifying enzyme originated from a microorganism of the genus *Acremonium*, β-xylosidase originated from *Thermotoga maritima* (by Thermostable Enzyme Laboratory Co., Ltd.) was added as the second saccharifying enzyme to an effective protein concentration of 0.2% by mass with respect to the total amount of the suspension to prepare a substrate-saccharifying enzyme mixture. The added saccharifying enzymes are shown in Table 1.

The substrate-saccharifying enzyme mixture was so used as to make the final concentration of the ammonia-treated rice straw as the substrate at 26% by mass.

The effective protein concentration can be measured using a protein quantifying reagent (by Nacalai Tesque Inc., Trade name: Protein Assay CBB Solution) by the Bradford method.

Next, the substrate-saccharifying enzyme mixture was maintained at a temperature of 50° C. for 3 days for a saccharifying reaction to obtain a saccharified solution. The concentration of xylose in the obtained saccharified solution was analyzed quantitatively using a liquid chromatography column (by Bio-Rad Laboratories. Inc., Trade name: HPX-87P) by high performance liquid chromatography. The result is shown in FIG. 3.

Figure 3:
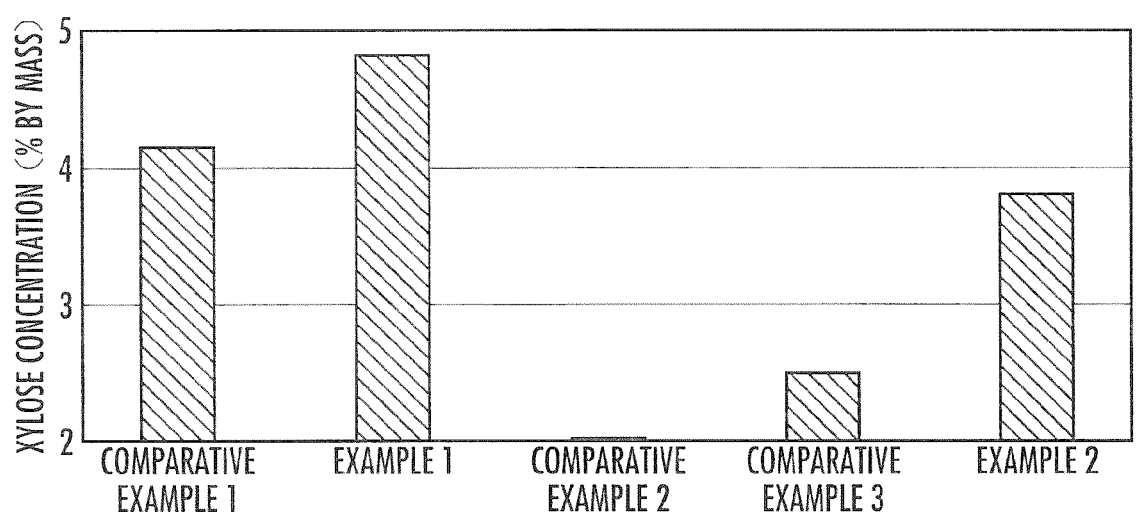
FIG. 3 is a graph showing the production amounts of xylose in saccharified solutions obtained by the production process according to the present invention.

The expression "TM" in FIG. 3 means β-xylosidase originated from *Thermotoga maritima*, the expression "Acremo" means a saccharifying enzyme originated from a microorganism of the genus *Acremonium*, and the expression "GC220" means a saccharifying enzyme originated from a microorganism of the genus *Trichoderma*.

Example 2

In the current Example, a saccharified solution was obtained identically with the Example 1, except that a saccharifying enzyme originated from a microorganism of the genus *Trichoderma* (by Genencor, a division of Danisco US Inc. Trade name: GC220) substituted for the saccharifying enzyme originated from a microorganism of the genus *Acremonium* as the first saccharifying enzyme and was added to an effective protein concentration of 0.9% by mass with respect to the total amount of the suspension. The added saccharifying enzymes are shown in Table 1.

Then the concentration of xylose in the obtained saccharified solution was analyzed quantitatively identically with Example 1. The result is shown in FIG. 3.

Comparative Example 1

In the current Comparative Example, a saccharified solution was obtained identically with the Example 1, except that only the saccharifying enzyme originated from a microorganism of the genus *Acremonium* as the first saccharifying enzyme was used and the β-xylosidase originated from *Thermotoga maritima* as the second saccharifying enzyme was not used at all. The added saccharifying enzyme is shown in Table 1.

Then the concentration of xylose in the obtained saccharified solution was analyzed quantitatively identically with Example 1. The result is shown in FIG. 3.

Comparative Example 2

In the current Comparative Example, a saccharified solution was obtained identically with the Example 1, except that only the β-xylosidase originated from *Thermotoga maritima* as the second saccharifying enzyme was used and the saccharifying enzyme originated from a microorganism of the genus *Acremonium* as the first saccharifying enzyme was not used at all. The added saccharifying enzyme is shown in Table 1.

Then the concentration of xylose in the obtained saccharified solution was analyzed quantitatively identically with Example 1. The result is shown in FIG. 3.

Comparative Example 3

In the current Comparative Example, a saccharified solution was obtained identically with the Example 1, except that only the saccharifying enzyme originated from a microorganism of the genus *Trichoderma* as the first saccharifying enzyme was used and the β-xylosidase originated from *Thermotoga maritima* as the second saccharifying enzyme was not used at all. The added saccharifying enzyme is shown in Table 1.

Then the concentration of xylose in the obtained saccharified solution was analyzed quantitatively identically with Example 1. The result is shown in FIG. 3.

TABLE 1

|  | First saccharifying enzyme (% by mass) | | Second saccharifying enzyme (% by mass) |
| --- | --- | --- | --- |
|  | Acremo | GC220 | β-xylosidase |
| Example 1 | 1.1 | — | 0.2 |
| Example 2 | — | 0.9 | 0.2 |
| Comparative Example 1 | 1.1 | — | — |
| Comparative Example 2 | — | — | 0.2 |
| Comparative Example 3 | — | 0.9 | — |

Acremo: Saccharifying enzyme originated from a microorganism of the genus *Acremonium*
GC220: Saccharifying enzyme originated from a microorganism of the genus *Trichoderma*

As obvious from FIG. 3, in case a mixture of the saccharifying enzyme originated from a microorganism of the genus *Acremonium* or the saccharifying enzyme originated from a microorganism of the genus *Trichoderma* as the first saccharifying enzyme and the β-xylosidase originated from *Thermotoga maritima* as the second saccharifying enzyme is used (Examples 1 and 2), xylose can be produced at a high yield, which is more than the total of the xylose produced using either of the first saccharifying enzymes alone (Comparative Examples 1 and 3), and the xylose produced using the second saccharifying enzyme alone (Comparative Example 2).

Example 3

In the current Example, a saccharified solution was obtained identically with the Example 1, except that the added amount of the β-xylosidase originated from *Thermotoga maritima* as the second saccharifying enzyme was changed so that the effective protein concentration thereof should fall within the range of 0.00002 to 10% by mass with respect to the total amount of the suspension.

Then the concentration of xylose in the obtained saccharified solution was analyzed quantitatively identically with Example 1. The concentration of the produced xylose in relation to the added amount of the β-xylosidase originated from *Thermotoga maritima* is shown in FIG. 4(*a*).

Figure 4:
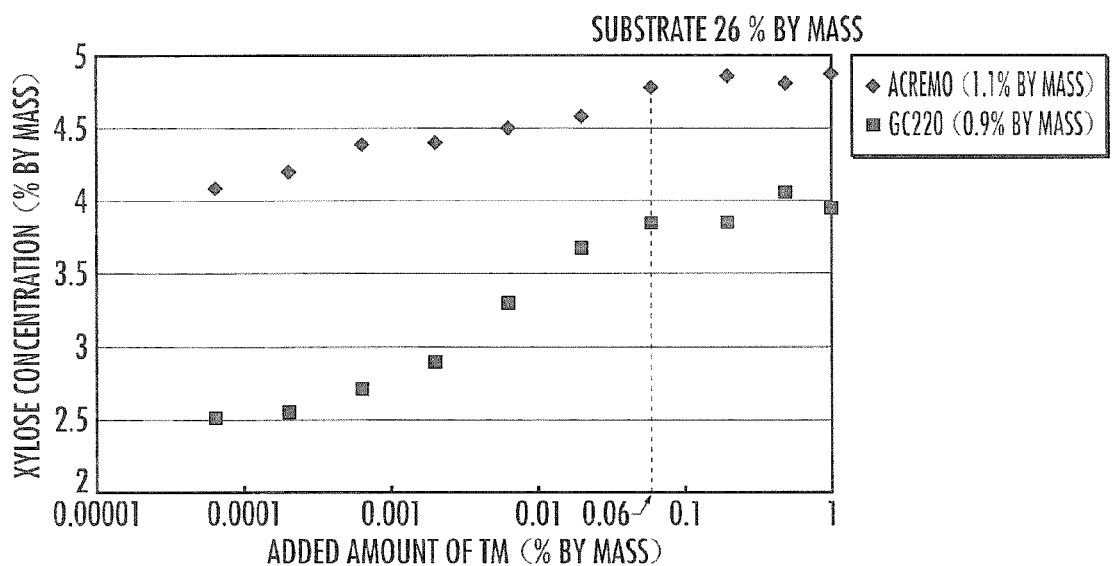
FIG. 4 is a graph showing the relationship between the production amount of xylose and the added amount of the second saccharifying enzyme to the first saccharifying enzyme.
Figure 4:
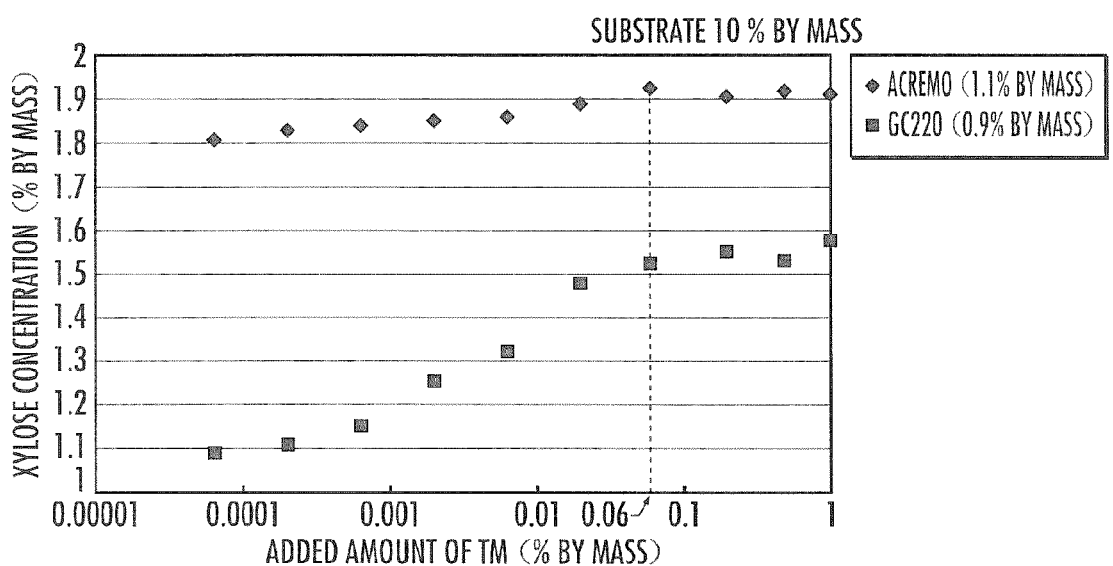

The expression "TM" in FIG. 4 means β-xylosidase originated from *Thermotoga maritima*, the expression "Acremo" means a saccharifying enzyme originated from a microorganism of the genus *Acremonium* and the expression "GC220" means a saccharifying enzyme originated from a microorganism of the genus Trichoderma.

Example 4

In the current Example, a saccharified solution was obtained identically with the Example 3, except that a saccharifying enzyme originated from a microorganism of the genus *Trichoderma* substituted for the saccharifying enzyme originated from a microorganism of the genus *Acremonium* as the first saccharifying enzyme and was added to an effective protein concentration of 0.9% by mass with respect to the total amount of the suspension.

Then the concentration of xylose in the obtained saccharified solution was analyzed quantitatively identically with Example 1. The concentration of the produced xylose in relation to the added amount of the β-xylosidase originated from *Thermotoga maritima* is shown in FIG. 4(*a*).

Example 5

In the current Example, a saccharified solution was obtained identically with the Example 3, except that the substrate-saccharifying enzyme mixture was so used as to make the final concentration of the ammonia-treated rice straw as the substrate at 10% by mass.

Then the concentration of xylose in the obtained saccharified solution was analyzed quantitatively identically with Example 1. The concentration of the produced xylose in relation to the added amount of the β-xylosidase originated from *Thermotoga maritima* is shown in FIG. 4(*b*).

Example 6

In the current Example, a saccharified solution was obtained identically with the Example 3, except that the substrate-saccharifying enzyme mixture was so used as to make the final concentration of the ammonia-treated rice straw as the substrate at 10% by mass, and that as the first saccharifying enzyme a saccharifying enzyme originated from a microorganism of the genus *Trichoderma* substituting for the saccharifying enzyme originated from a microorganism of the genus *Acremonium* was added to an effective protein concentration of 0.9%) by mass with respect to the total amount of the suspension.

Then the concentration of xylose in the obtained saccharified solution was analyzed quantitatively identically with Example 1. The concentration of the produced xylose in relation to the added amount of the β-xylosidase originated from *Thermotoga maritima* is shown in FIG. 4(*b*).

As obvious from FIG. 4, in case the concentration of the substrate in the substrate-saccharifying enzyme mixture is 10% by mass or 26% by mass; the concentration of the saccharifying enzyme originated from a microorganism of the genus *Acremonium* as the first enzyme is 1.1% by mass, or the concentration of the saccharifying enzyme originated from a microorganism of the genus *Trichoderma* as the first enzyme is 0.9% by mass; xylose can be produced at a high yield by selecting the concentration of the β-xylosidase originated from *Thermotoga maritima* as the second saccharifying enzyme in the range of 0.06 to 1.0% by mass.

What is claimed is:

1. A process for producing a saccharified solution of lignocellulosic biomass, the process comprising preparation of a pretreated material for saccharification by pretreating lignocellulosic biomass as a substrate to dissociate lignin contained in the lignocellulosic biomass or swell the lignocellulosic biomass, and a saccharifying treatment of a substrate-saccharifying enzyme mixture obtained by adding a saccharifying enzyme produced by a microorganism to the pretreated material for saccharification with the saccharifying enzyme to produce a saccharified solution, wherein the saccharifying enzyme is a mixture of a first saccharifying enzyme originated from one or more microorganisms selected from the group consisting of fungi of the genus *Acremonium*, the genus *Trichoderma*, the genus *Penicillium*, the genus *Aspergillus* and the genus *Thermoascus*, and eubacteria of the genus *Clostridium* and the genus *Bacillus*, and a second saccharifying enzyme comprising β-xylosidase originated from *Thermotoga maritime*, the substrate-saccharifying enzyme mixture contains the substrate at a concentration in a range of 10 to 26% by mass, and the substrate-saccharifying enzyme mixture contains the first saccharifying enzyme at a concentration in a range of 0.1 to 10% by mass, and the second saccharifying enzyme at a concentration in a range of 0.06 to 1.0% by mass.

2. The process for producing a saccharified solution of lignocellulosic biomass according to claim 1, wherein rice straw is used as the lignocellulosic biomass which is the substrate.

3. The process for producing a saccharified solution of lignocellulosic biomass according to claim 1, wherein a saccharifying enzyme originated from a microorganism of the genus *Acremonium* is added as the first saccharifying enzyme.

4. The process for producing a saccharified solution of lignocellulosic biomass according to claim 1, wherein a saccharifying enzyme originated from a microorganism of the genus *Trichoderma* is added as the first saccharifying enzyme.

5. The process for producing a saccharified solution of lignocellulosic biomass according to claim 1, wherein ammonia water is mixed with the lignocellulosic biomass as the substrate in the pretreatment, and the obtained substrate mixture is maintained at a temperature in a range of 20 to 100° C. for a duration in a range of 0.5 to 24 hours to react the lignocellulosic biomass with the ammonia water.

6. The process for producing a saccharified solution of lignocellulosic biomass according to claim 1, wherein ammonia water is mixed with the lignocellulosic biomass as the substrate in the pretreatment, and the obtained substrate mixture is maintained at a temperature of 80° C. for 8 hours to react the lignocellulosic biomass with the ammonia water.

7. The process for producing a saccharified solution of lignocellulosic biomass according to claim 1, wherein the substrate-saccharifying enzyme mixture contains the first saccharifying enzyme at a concentration in a range of 0.9 to 1.1% by mass, and the second saccharifying enzyme at a concentration in a range of 0.06 to 1.0% by mass.

8. The process for producing a saccharified solution of lignocellulosic biomass according to claim 1, wherein the substrate-saccharifying enzyme mixture is maintained at a temperature in a range of 20 to 60° C. for a duration in a range of 24 to 240 hours in the saccharifying treatment.

9. The process for producing a saccharified solution of lignocellulosic biomass according to claim 1, wherein the substrate-saccharifying enzyme mixture is maintained at a temperature of 50° C. for 3 days in the saccharifying treatment.

* * * * *